(12) United States Patent
Soubelet et al.

(10) Patent No.: US 8,718,338 B2
(45) Date of Patent: May 6, 2014

(54) SYSTEM AND METHOD TO COMPENSATE FOR RESPIRATORY MOTION IN ACQUIRED RADIOGRAPHY IMAGES

(75) Inventors: Elisabeth Soubelet, Meudon (FR); Jean Lienard, Igny (FR); Regis Vaillant, Villebon sur Yvette (FR)

(73) Assignee: General Electric Company, Schenectady, NY (US)

( * ) Notice: Subject to any disclaimer, the term of this patent is extended or adjusted under 35 U.S.C. 154(b) by 1012 days.

(21) Appl. No.: 12/508,070

(22) Filed: Jul. 23, 2009

(65) Prior Publication Data

US 2011/0019878 A1 Jan. 27, 2011

(51) Int. Cl.
G06K 9/00 (2006.01)
A61B 5/05 (2006.01)
A61B 6/00 (2006.01)
G01N 23/00 (2006.01)
A61B 6/08 (2006.01)

(52) U.S. Cl.
USPC ........... 382/128; 382/103; 600/431; 600/407; 378/20; 378/205

(58) Field of Classification Search
None
See application file for complete search history.

(56) References Cited

U.S. PATENT DOCUMENTS

| 5,602,891 | A * | 2/1997 | Pearlman ..................... 378/62 |
| 7,421,061 | B2 | 9/2008 | Boese et al. |
| 7,831,074 | B2 * | 11/2010 | Zhou et al. ..................... 382/128 |
| 8,155,739 | B2 * | 4/2012 | Keel et al. ........................ 607/9 |
| 8,170,307 | B2 * | 5/2012 | Karmonik et al. ............ 382/128 |
| 8,180,130 | B2 * | 5/2012 | Sebok ............................ 382/128 |
| 8,295,911 | B2 * | 10/2012 | Heigl ............................. 600/424 |
| 2006/0155184 | A1 * | 7/2006 | Florent et al. ................ 600/407 |
| 2007/0060799 | A1 * | 3/2007 | Lyon et al. .................... 600/300 |
| 2007/0066881 | A1 * | 3/2007 | Edwards et al. .............. 600/407 |
| 2007/0238947 | A1 | 10/2007 | Pescatore et al. |
| 2007/0247454 | A1 | 10/2007 | Rahn et al. |
| 2007/0270689 | A1 | 11/2007 | Lothert |
| 2008/0240536 | A1 | 10/2008 | Soubelet et al. |
| 2008/0267490 | A1 | 10/2008 | Gorges et al. |
| 2009/0012390 | A1 | 1/2009 | Pescatore et al. |
| 2009/0149741 | A1 * | 6/2009 | Heigl ............................. 600/424 |
| 2009/0220132 | A1 | 9/2009 | Trousset et al. |
| 2009/0299424 | A1 * | 12/2009 | Narayan ........................... 607/9 |
| 2011/0112403 | A1 * | 5/2011 | Machtey et al. .............. 600/443 |
| 2011/0184276 | A1 * | 7/2011 | Lyon et al. .................... 600/424 |

* cited by examiner

Primary Examiner — Randolph I Chu

(57) ABSTRACT

A system and method to compensate for respiratory motion in imaging of instruments introduced into the subject anatomy is provided. The system can include an imaging system in communication with a controller. The controller can include a memory with program instructions for execution by the processor to perform the steps of: detecting an illustration of at least a portion of the plurality of instruments introduced into the subject anatomy in a first image and a second image, comparing and calculating a displacement of the plurality of instruments between the first and second images, calculating one of an average or median displacement of the plurality of instruments between the first and second images, and applying one of the average and the median displacement to adjust at least a portion of the first or second images or a pre-acquired three-dimensional model of the internal region of interest.

17 Claims, 2 Drawing Sheets

SYSTEM AND METHOD TO COMPENSATE FOR RESPIRATORY MOTION IN ACQUIRED RADIOGRAPHY IMAGES

BACKGROUND

The subject matter described herein relates to detecting and compensating for respiratory motion in radiography images, in particular in regard to the field of cardiology.

Use of radiological imaging is known in the diagnosis and treatment of cardiac pathologies. The treatment may include electrophysiology, and other interventional procedures, etc. For example, in a certain number of interventional procedures, the practitioner can pass several catheters and/or guides into vessels or cavities of the heart. These interventional procedures include different techniques such as embolization, dilation, desobstruction, placing of stents, and ablation. These procedures make it possible to avoid heavy surgical intervention.

During a typical known interventional procedure, the operator can guide the operating tool chiefly through illustration of anatomical structures in the acquired radiography images.

BRIEF SUMMARY

The subject matter addresses the above-described drawbacks and needs. A system and method is provided to detect and compensate for respiratory motion through acquired radiography images.

According to one embodiment, a method to compensate for respiratory motion in imaging of a subject anatomy is provided. The method comprises acquiring a first image of an internal region of interest of the subject anatomy; detecting an illustration of at least a portion of a plurality of instruments introduced into the subject anatomy in the first image; acquiring a second image of the internal region of interest of the subject anatomy; detecting an illustration in the second image of at least the portion of a plurality of instruments introduced into the subject anatomy; comparing and calculating a displacement in the illustrations of at least the portion of the plurality of instruments between the first image and the second image, calculating one of an average or median displacement of at least the portion of the plurality of instruments between the first and second images, and applying one of the average and the median displacement to adjust at least a portion of one of the following: the acquired image data of the first or second images or a pre-acquired three-dimensional model of the internal region of interest, wherein the applying step creates a display compensated for respiratory motion of the internal region of interest.

According to another embodiment, a system to compensate for respiratory motion in imaging of a subject anatomy is provided. The system comprises a plurality of instruments introduced into the subject anatomy; an imaging system operable to acquire a first and a second image of the plurality of instruments introduced into the subject anatomy; and a controller in communication with the imaging system, the controller including a processor in communication with a memory, the memory including a plurality of program instructions for execution by the processor to perform the steps of: detecting an illustration of at least a portion of the plurality of instruments introduced into the subject anatomy in the first image, detecting an illustration in the second image of at least the portion of the plurality of instruments introduced into the subject anatomy, comparing and calculating a displacement in the illustrations of at least the portion of the plurality of instruments between the first image and the second image, calculating one of an average or median displacement of the plurality of instruments between the first and second images, and applying one of the average and the median displacement to adjust at least a portion of one of the following: the acquired image data of the first or second images or a pre-acquired three-dimensional model of the internal region of interest, wherein the applying step creates a display compensated for respiratory motion of the internal region of interest.

According to yet another embodiment, a system to compensate for respiratory motion in imaging of a subject anatomy is provided. The system comprises a plurality of instruments introduced into the subject anatomy; an imaging system operable to acquire a first and a second image of the plurality of instruments introduced into the subject anatomy; and a controller in communication with the imaging system, the controller including a processor in communication with a memory, the memory including a plurality of program instructions for execution by the processor to perform the steps of: detecting an illustration of at least a portion of the plurality of instruments introduced into the subject anatomy in the first image, detecting an illustration in the second image of at least the portion of the plurality of instruments introduced into the subject anatomy, comparing and calculating a displacement in the illustrations of at least the portion of the plurality of instruments between the first image and the second image, calculating one of an average or median displacement of the plurality of instruments between the first and second images, and applying one of the average or median displacement of the plurality of instruments to adjust the image data of a pre-acquired three-dimensional model of the internal region of interest to create a display of the displacement illustrative of the internal region of interest compensated for respiratory motion.

Systems and methods of varying scope are described herein. In addition to the aspects of the subject matter described in this summary, further aspects of the subject matter will become apparent by reference to the drawings and with reference to the detailed description that follows.

BRIEF DESCRIPTION OF THE DRAWINGS

The invention will be understood more clearly from the following description and the single accompanying figure. This figure is given by way of an indication and in no way restricts the scope of the invention.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Figure 1:
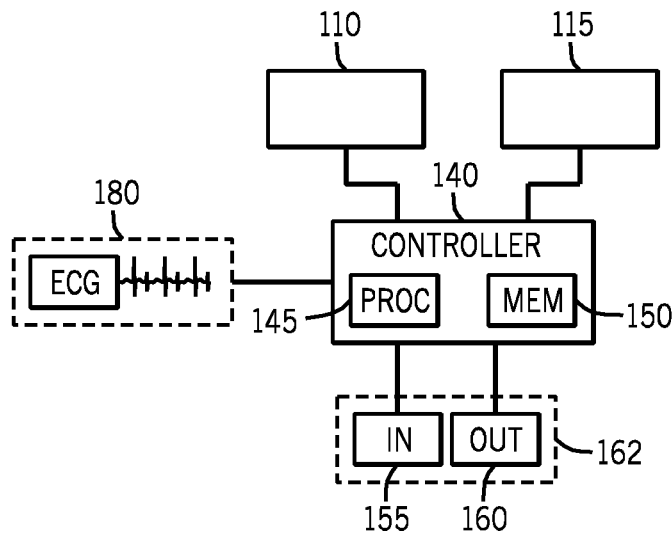
FIG. 1 shows a schematic diagram to illustrate an embodiment of a system according to the subject matter described herein.
Figure 3:
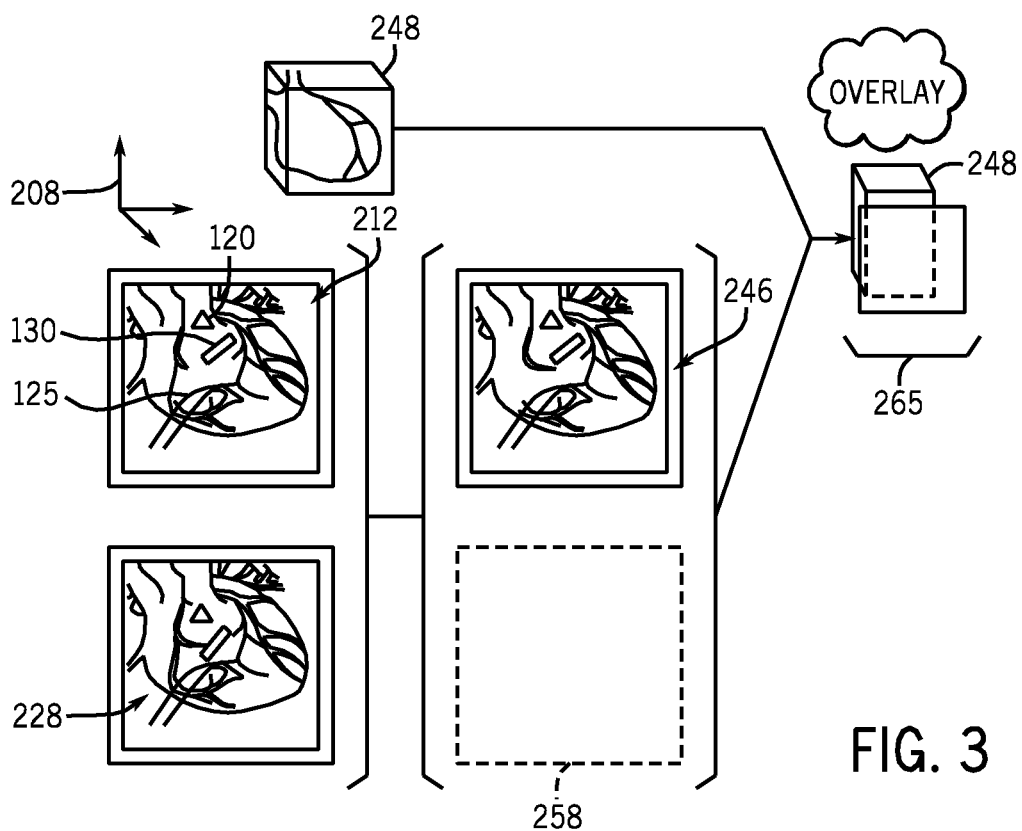
FIG. 3 shows a schematic diagram illustrative of an embodiment of analysis of respiratory motion in acquired radiology images using the system of FIG. 1 and the method of FIG. 2.

FIG. 1 illustrates a system 100 to compensate for respiratory motion in acquired radiography imaging or three-dimensional modeling of a subject or patient anatomy 105 in accordance with the subject matter described herein. The system 100 can be used, for example, in a medical intervention procedure with a patient anatomy (e.g., procedure on the heart such as the ablation of atrial fibrillation, or in a biventricular procedure).

One embodiment of the system 100 can comprise both a three-dimensional (3D) imaging system 110 and a radiography imaging system 115. The 3D imaging system 110 may be, inter alia, a computerized tomography (CT) machine, a radiography system taking 3D images by rotation, magnetic resonance systems, positron-emission tomography (PET), ultrasonic systems, nuclear medicine systems or combination thereof. The radiography imaging system 115 may be independent of or integrated with the 3D imaging system 110. Examples of the radiography imaging system 115 can be an x-ray system, a positron emission tomography (PET) system, a computerized tomosynthesis (CT) system, an angiographic or fluoroscopic system, and the like or combination thereof. The 3D imaging system 110 or radiography imaging system 115 can be operable to generate static images acquired by static imaging detectors (e.g., CT systems, MRI systems, etc.) prior to a medical procedure, or real-time images acquired with real-time imaging detectors (e.g., angioplastic systems, laparoscopic systems, endoscopic systems, etc.) during the medical procedure. Thus, the types of acquired images can be diagnostic or interventional.

The system 100 can also include a series of instruments 120, 125, 130 introduced into the patient anatomy 105. Examples of instruments 120, 125, 130 can include sensors, leads attached at the organ or region of interest (e.g., heart), markers, catheters, guidewires, or combination thereof.

An embodiment of the system 100 also includes a controller 140 in communication with the radiography imaging system 115 and the 3D imaging system 110. An embodiment of the controller 140 includes a processor 145 in communication with a memory 150. The processor 145 can be arranged independent of or integrated with the memory 150. Although the processor 145 and memory 150 can be described located at the controller 140, it should be understood that the processor 145 or memory 150 or portion thereof can be located at the 3D imaging system 110 or radiological imaging system 115.

The processor 145 can be generally operable to execute the program instructions representative of acts or steps described herein and stored in the memory 150. The processor 145 can also be capable of receiving input data or information or communicating output data. Examples of the processor 145 can include a central processing unit of a desktop computer, a microprocessor, a microcontroller, or programmable logic controller (PLC), or the like or combination thereof.

An embodiment of the memory 150 generally comprises one or more computer-readable media operable to store a plurality of computer-readable program instructions for execution by the processor 145. The memory 150 can also operable to store data generated or received by the controller 140. By way of example, such media may comprise RAM, ROM, PROM, EPROM, EEPROM, Flash, CD-ROM, DVD, or other known computer-readable media or combinations thereof which can be used to carry or store desired program code in the form of instructions or data structures and which can be accessed by a general purpose or special purpose computer or other machine with a processor.

The controller 140 further includes or is in communication with an input device 155 and an output device 160. The input device 155 can be generally operable to receive and communicate information or data from user to the controller 140. The input device 155 can include a mouse device, pointer, keyboard, touch screen, microphone, or other like device or combination thereof capable of receiving a user directive. The output device 160 can be generally operable to illustrate output data for viewing by the user. An embodiment of the output device 160 can be operable to simultaneously illustrate or fuse static or real-time image data generated by the 3D imaging system 110 or radiological imaging system 115. The output device 160 is capable of illustrating two-dimensional, three-dimensional image and/or four-dimensional image data or combination thereof through shading, coloring, and/or the like. Examples of the output device 160 include a cathode ray monitor, a liquid crystal display (LCD) monitor, a touch-screen monitor, a plasma monitor, or the like or combination thereof. An embodiment of the input device 155 and output device 160 can be integrated on a touch-screen interface (illustrated in dashed line and reference 162). Embodiments of at least a portion of the input device 155 or a portion of the output device 160 can be integrated with the 3D imaging system 110 or the radiological imaging system 115.

According to another embodiment the system 100, the three-dimensional (3D) imaging system 110 and the radiography imaging system 115 and the controller 140 can be connected in communication with an electrocardiogram (ECG) system 180 to enable ECG gated image acquisition of the subject anatomy 105 in a known manner.

Figure 2:
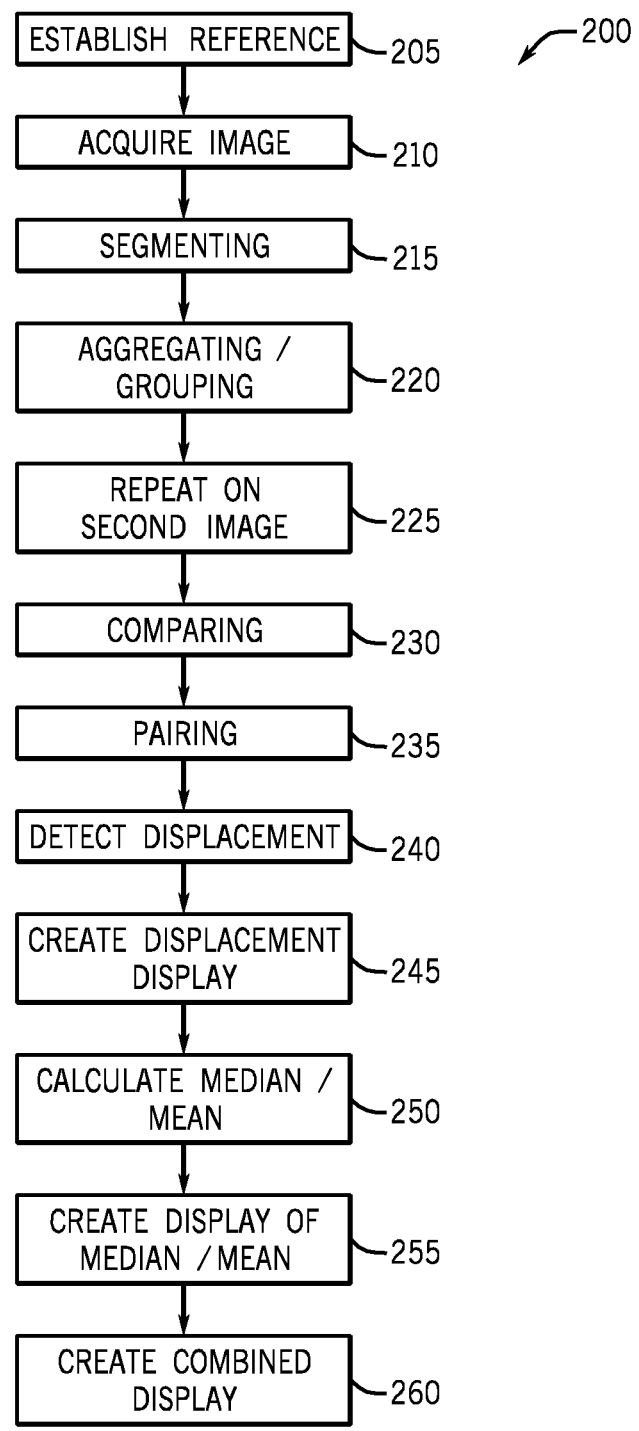
FIG. 2 includes a flow diagram illustrative of an embodiment of a method to compensate for respiratory motion using the system of FIG. 1.

Having provided a description of the general construction of the system 100, the following is a description of a method 200 (see FIG. 2) of operation of the system 100 in relation to the imaged patient anatomy 105. Although an exemplary embodiment of the method 200 is discussed below, it should be understood that one or more acts or steps comprising the method 200 could be omitted or added. It should also be understood that one or more of the acts can be performed simultaneously or at least substantially simultaneously, and the sequence of the acts can vary. Furthermore, it is embodied that at least several of the following steps or acts can be represented as a series of computer-readable program instructions to be stored in the memory 150 of the controller 140 for execution by the processor 145 or one or more of the 3D imaging system 110 or the radiography imaging system 115.

Step 205 includes establishing or defining a common reference system 208. To this end, an existing algorithm is performed for determining an acquisition geometry as a function of parameters of the radiography imaging system 115. The acquisition geometry of the radiological system 110 can be relative to a positioning of the tube (not shown) and of the detector (not shown) in the common reference system 208. For example, this acquisition geometry can be defined both by the position in space of a pillar (of the X-ray apparatus and that of an examination table (not shown) on which the patient reclines, relative to the common reference system 208. The common reference system 208 can enable a reference link to be set up between the 3D imaging system 10 and the radiography imaging system 115, thereby interlinking of items of geometrical information that are known and belong to each image acquisition system 110 and 115.

Step 210 can include acquiring at least one radiography image 212 at a time (t). One embodiment of the radiography image 212 can be acquired via fluoroscopy.

Step 215 includes segmenting the acquired image data in image 212. The segmenting step 215 can include applying a low pass filter or other algorithm to remove background image data from the image 212 in a manner so as to isolate image data associated with one or more instruments 120, 125, 130 illustrated therein. For example, step 215 can include removing or clearing the image elements or pixels illustrative of features other than the instruments 120, 125, 130 in the image 212. For example, the image elements illustrative of features having a thickness larger than the diameter of a catheter, in the case when one of the instruments 120, 125, 130 includes the catheter.

Step 220 can include aggregating or grouping of image data or pixels associated with the one or more instruments 120, 125, 130 in image 212. An embodiment of the aggregating step 220 can include acquiring instructions of a geometry, size, gray-scale level value, alignment, or distance relative a landmark for each of the one or more instruments 120, 125, 130 illustrated in image 212. Based on the acquired instructions, the aggregating step 220 can include grouping or aggregating image data associated with each of the one or more instruments 120, 125, 130 in the image 212.

An example of step 220 can include filtering or analyzing each image element or pixel of the image 212 such that each pixel or image element of the image 212 can be associated with a certain probability of belonging to a linear segment of one or more of the instruments 120, 125, 130 (e.g., guidewire, catheter, etc.). The step 220 can further include creating a map of the calculated probabilities of the image elements illustrative of the instruments 120, 125, 130 and correlating to the image 212 so as to create an illustration of a set of image elements having a threshold or increased probability of representing the instruments the 120, 125, 130.

Step 225 can include repeating the image acquisition step 210 to acquire a second image 228 of the patient anatomy acquired at a second time (t+n) and applying the segmenting step 215 and the aggregating step 220 with respect thereto. An embodiment of steps 210 and 225 can include acquisition of the successive images 212, 228 in combination with electrocardiogram (ECG) gating so as to minimize effects associated with cardiac-induced motion. Thereby, displacement in the acquired image data between the succession of images 212, 228 can generally be associated as caused by respiratory motion. The embodiment of step 225 can include applying the same segmentation and image analyses described above in steps 215 and 220 to group or aggregate image data associated with each of the one or more instruments 120, 125, 130 in the image 228.

Step 230 can include comparing and identifying image elements or pixels between the images 212, 228. Step 235 can include grouping or pairing image elements or pixels in one image associated with each respective instrument with image elements or pixels associated with the same instrument in the other image. An embodiment of the pairing step 235 can be performed based on same parameters (e.g., a geometry, size, gray-scale level value, alignment, or distance of each of the one or more instruments 120, 125, 130 relative to a landmark, probabilities) as described above with respect to step 220. The image analysis of steps 230 and 235 to perform comparing and grouping can be performed automatically based on whatever the number of instruments 120, 125, and 130 are located in the subject anatomy 105.

Step 240 can include applying an algorithm to detect or calculate an occurrence of respiratory motion or displacement or translation between the acquired image elements of one or more of the instruments 120, 125, 130 in image 212 relative to the acquire image elements of the one or more of the instruments 120, 125, 130 in image 228. An embodiment of step 240 can include measuring the displacement or translation of pairing of the image elements according to step 235 for each of the instruments 120, 125, and 130 between the images 212 acquired at time (t) relative to the image 228 acquired at time (t+n). The measure of the displacement can be correlated to a shift or change in location of image elements relative to the reference 208.

Step 245 can include creating a translation or displacement display or map 246 illustrative of the motion, translation, or displacement of image illustration of one or more of the instruments 120, 125, and 130 from a duration between time (t) through time (t+n) in one or more of the first image 212, the second image 228. Another embodiment of the map 246 can comprise motion, translation, or displacement of image illustration of a pre-acquired three-dimensional volume or model 248 of the internal region of interest of the subject anatomy 105. The duration can vary depending on the time of acquisition and the number of succession of images 212, 228 acquired. The display or map 248 can be illustrated over a time sequence to show motion of the imaged anatomy 105 associated with respiration.

Step 250 can include calculating at least one of a mean or median of the motion, translation or displacement of the combination of instruments 120, 125 and 130 over the duration from time (t) to time (t+n) in one or more of the first image 212, the second image 228, or a pre-acquired three-dimensional model 248 of the internal region of interest of the subject anatomy 105.

Step 255 can include creating a display or map 258 illustrative of the mean or median location of the image elements of the subject anatomy 105 between time (t) and time (t+n). An embodiment of the system 100 and method 200 applies the mean or median displacement calculated in step 250 to adjust or displace at least a portion of the image data in at least one of the acquired images 112 or 228. Another embodiment of the map 258 can comprise mean or median displacement of at least a portion of the image data of the pre-acquired three-dimensional model 248 of the internal region of interest of the subject anatomy 105.

Step 260 can include generating or creating a combined display 265 for illustration to the user. One embodiment of the combined display 260 includes the display or map 258 illustrative of the displaced mean or median location of the acquired image elements of images 212 and/or 228 between time (t) and time (t+n) according to step 255 and applying in fusion, combination or overlay arrangement with a two-dimensional projection of the 3D model or the 3D model 248 itself of the subject anatomy 105. Another embodiment of the combined display 265 includes the display of the displacement map 248 created as described in step 255 in combination, overlay or fusion arrangement with a two-dimensional projection of the 3D model or the 3D model 248 itself of the subject anatomy 105.

According to yet another embodiment, the combined display 265 can include the 3D volume or model 248 geometrically correctly positioned and fused on the image 212. Upon acquisition of image data of the image 228 and calculation of the respiratory displacement between images 212 and 228 as described in step 240, the respiratory displacement can be then applied to adjust the image elements of the 3D model 248 before fusion with the image 228 and so on for any image acquired subsequent to image 212 so as to compensate for respiratory motion.

A technical effect of the above-described system 100 and method 200 can provide compensation for respiratory motion without use of supplemental tracking hardware. The system and method can provide compensation for respiratory motion via application of an image processing algorithm on acquired image data of the subject anatomy. The system 100 and method 200 can use the instruments 120, 125, 130 introduced in the heart or surrounding anatomy in order to compute these motions and compensate them. The more instruments 120, 125, 30 introduced in the subject anatomy, the more accurate can be the compensation for respiratory motion. Furthermore, even if a physician moves an instrument 120, 125, 130 inside the heart, the motion introduced by the physician can be offset or minimized in the overall computed compensation for respiratory motion because multiple instruments 120, 125, 130 are introduced in the subject anatomy.

This written description uses examples to disclose the subject matter, including the best mode, and also to enable any person skilled in the art to make and use the subject matter described herein. Accordingly, the foregoing description has been presented for the purpose of illustration and description, and is not intended to be exhaustive or to limit the subject matter to the precise form disclosed, and modifications and variations are possible in light of the above teachings or may be acquired from practice of the subject matter described herein. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method to compensate for respiratory motion in imaging of a subject anatomy, the method comprising:
   acquiring a first image of an internal region of interest of the subject anatomy;
   detecting an illustration of at least a portion of a plurality of instruments introduced into the subject anatomy in the first image;
   acquiring a second image of the internal region of interest of the subject anatomy;
   detecting an illustration in the second image of at least the portion of a plurality of instruments introduced into the subject anatomy;
   comparing and calculating a displacement in the illustrations of at least the portion of the plurality of instruments between the first image and the second image,
   calculating one of an average or median displacement of at least the portion of the plurality of instruments between the first and second images, and
   applying one of the average and the median displacement to adjust at least a portion of one of the following: the acquired image data of the first or second images or a pre-acquired three-dimensional model of the internal region of interest,
   wherein the applying step creates a display compensated for respiratory motion of the internal region of interest.

2. The method of claim 1, further comprising the step of:
   registering the display of one of the first and second images of the internal region of interest compensated for respiratory motion with one of a two-dimensional projection of a three-dimensional model of the internal region of interest and the three-dimensional model of the internal region of interest.

3. The method of claim 1, further comprising the step of:
   applying the displacement in the illustrations of at least the portion of the plurality of instruments to the acquired image data of the first and second images to create an image of the internal region of interest in motion over the time period between the acquisition of the first and second images.

4. The method of claim 3,
   registering one of the first and second images of the internal region of interest in motion with one of the two-dimensional projection of the three-dimensional model of the internal region of interest or the three-dimensional model of the internal region of interest.

5. The method of claim 1, further comprising the step of:
   grouping one or more image elements of the illustration of at least a portion of the plurality of instruments in the first image with one or more image elements of the illustration of at least the portion of each of the associated plurality of instruments in the second image, wherein the step of calculating the displacement is applied to each grouping of one or more image elements of the illustration of at least the portion of the associated plurality of instruments.

6. The method of claim 5, wherein the step of grouping is based on one or more of the following parameters: a geometry, a size, a gray-scale level, an alignment, or distance from a reference associated with the acquired image elements associated with at least the portion of the plurality of instruments.

7. The system of claim 1, wherein the steps of acquiring the first and second images includes electrocardiogram (ECG) gating in the acquiring of the first and second images.

8. A system to compensate for respiratory motion in imaging of a subject anatomy, comprising:
   a plurality of instruments introduced into the subject anatomy;
   an imaging system operable to acquire a first and a second image of the plurality of instruments introduced into the subject anatomy; and
   a controller in communication with the imaging system, the controller including a processor in communication with a memory, the memory including a plurality of program instructions for execution by the processor to perform the steps of:
      detecting an illustration of at least a portion of the plurality of instruments introduced into the subject anatomy in the first image,
      detecting an illustration in the second image of at least the portion of the plurality of instruments introduced into the subject anatomy,
      comparing and calculating a displacement in the illustrations of at least the portion of the plurality of instruments between the first image and the second image,
      calculating one of an average or median displacement of the plurality of instruments between the first and second images, and
      applying one of the average and the median displacement to adjust at least a portion of one of the following: the acquired image data of the first or second images or a pre-acquired three-dimensional model of the internal region of interest,
      wherein the applying step creates a display compensated for respiratory motion of the internal region of interest.

9. The system of claim 8, further including program instructions for execution by the processor to perform the step of:
   registering the display of the internal region of interest compensated for respiratory motion with one of a two-dimensional projection of a three-dimensional model of the internal region of interest or the three-dimensional model of the internal region of interest.

10. The system of claim 9, further including program instructions for execution by the processor to perform the step of:

applying the displacement in the illustrations of at least the portion of the plurality of instruments to the acquired image data of the first and second images to create an image of the region of interest in motion over the time period between the acquisition of the first and second images.

11. The system of claim 10, further including program instructions for execution by the processor to perform the step of:

registering the image of the region of interest in motion with one of the two-dimensional projection of the three-dimensional model of the internal region of interest or the three-dimensional model of the internal region of interest.

12. The system of claim 8, further including program instructions for execution by the processor to perform the step of:

grouping one or more image elements of the illustration of at least a portion of the plurality of instruments in the first image with one or more image elements of the illustration of at least the portion of the associated plurality of instruments in the second image, wherein the step of calculating the displacement is applied to each grouping of one or more image elements of the illustration of at least the portion of the associated plurality of instruments.

13. The system of claim 12, wherein the step of grouping is based on one or more of the following parameters: a geometry, a size, a gray-scale level, an alignment, or distance from a reference associated with the acquired image elements associated with at least the portion of the plurality of instruments.

14. The system of claim 8, wherein the imaging system employs electrocardiogram gating in acquiring the first and second images.

15. A system to compensate for respiratory motion in imaging of a subject anatomy, comprising:

a plurality of instruments introduced into the subject anatomy;

an imaging system operable to acquire a first and a second image of the plurality of instruments introduced into the subject anatomy; and a controller in communication with the imaging system, the controller including a processor in communication with a memory, the memory including a plurality of program instructions for execution by the processor to perform the steps of:

detecting an illustration of at least a portion of the plurality of instruments introduced into the subject anatomy in the first image, detecting an illustration in the second image of at least the portion of the plurality of instruments introduced into the subject anatomy, comparing and calculating a displacement in the illustrations of at least the portion of the plurality of instruments between the first image and the second image, calculating one of an average or median displacement of the plurality of instruments between the first and second images, and applying one of the average or median displacement of the plurality of instruments to adjust the image data of a pre-acquired three-dimensional model of the internal region of interest to create a display of the displacement illustrative of the internal region of interest compensated for respiratory motion.

16. The system of claim 15, wherein the display includes the 3D model of the internal region of interest adjust by applying one of the average or median displacement and fused with one of the first and second images.

17. The system of claim 15, wherein the imaging system is connected in communication with an electrocardiogram (ECG) system so as to perform ECG gating in acquisition of the first and second images.

* * * * *